United States Patent [19]

Szkolnik

[11] 4,391,813

[45] Jul. 5, 1983

[54] VAPOR PHASE FUNGICIDAL METHOD
[75] Inventor: Michael Szkolnik, Geneva, N.Y.
[73] Assignee: Cornell Research Foundation, Inc., Ithaca, N.Y.
[21] Appl. No.: 257,039
[22] Filed: Apr. 17, 1981
[51] Int. Cl.$^3$ ............................................. A01N 43/48
[52] U.S. Cl. .................................................... 424/269
[58] Field of Search ........................................ 424/269
[56] References Cited

U.S. PATENT DOCUMENTS 4,079,062  3/1978  Reet et al. .

OTHER PUBLICATIONS

*Phytopathology* 71: 908 (1981).
*Phytopathology* 72: 266 (1982).
*Plant Disease* 65: 981–985 (1981).
Bent, K. J., *Ann. Appl. Biol.*, 1967, 60:251–263.
Solel, Z., *Pestic. Sci.*, 1971, 2:126.
Hislop, E. C., *Ann. appl. Biol.*, 1967, 60:265–279.
Scheinpflug, H. and V. Paul, *Neth. J. Pl. Path.*, 1977, (Suppl. 1), 105–111.

Gilpatrick, J. D., and C. A. Smith, *Fungicide and Nematicide Tests* 1980, 35:30–31.
Hickey, K. D., Alice E. Davis, and Janice C. Scalza, *Fungicides and Nematicide Tests*, 1979, 34:6–7.
Szkolnik, Michael, *Spec. Report No.*, 1978, 28:22–27.
Szkolnik, Michael, *Annu. Rev. Phytopathol*, 1978, 16:103–129.
Szkolnik, Michael, *Phytophathology*, May 1980, 70:469.
Szkolnik, Michael, L. M. Henecke and J. R. Nevill, *Fungicide and Nematicide Tests*, 1980, 35:21–22.
Szkolnik, Michael, *Soc. Fungicides and Nematicide Tests*, 1981, 36:19.
Szkolnik, Michael, *Fungicide and Nematicide Tests, Apr. 24, 1980, 35:20.*

*Primary Examiner*—Leonard Schenkman
*Attorney, Agent, or Firm*—Jones, Tullar & Cooper

[57] ABSTRACT

This invention relates to the vapor phase treatment of plants with 1-($\beta$-aryl)ethyl-1H-1,2-4-triazole ketals to prevent or control microbial infestation, especially powdery mildews.

7 Claims, No Drawings

VAPOR PHASE FUNGICIDAL METHOD

BACKGROUND OF THE INVENTION

U.S. Pat. No. 4,079,062, hereby incorporated by reference in its entirety, describes the preparation of the compounds employed herein and their use as antimicrobial agents and plant growth regulators.

Scheinpflug et al, *Neth. J. Path.*, 83:105–111 (1977) report that triadimefon, i.e.

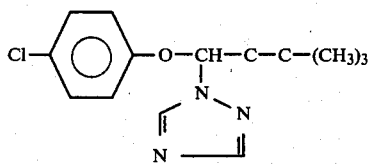

acts in the vapor phase against powdery mildew.

Beut, *Ann. appl. Biol.*, 60:251–263 (1967) also teach certain fungicides prevent powdery mildew by vapor effects.

Solel, *Pestic. Sci.*, 2:126 (1971) examined various fungicides for vapor action.

Hislop, *Ann. appl. Biol.*, 60:265–279 (1967) examined various fungicides for vapor action.

While a number of workers have noted vapor phase fungicidal activity over short distances, it appears that the results have varied and that fungicides having sufficient vapor phase activity for sustained practical use may be rare.

DESCRIPTION OF THE INVENTION

This invention relates to the vapor phase treatment of plants with 1-(β-aryl)ethyl-1H-1,2,3-triazole ketals to prevent or control microbial infestation, especially powdery mildews.

The compounds useful in this are described in U.S. Pat. No. 4,079,062, incorporated by reference and are 1H-1,2,4-triazole derivatives having the formula

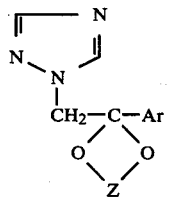

wherein Z is an alkylene selected from the group consisting of

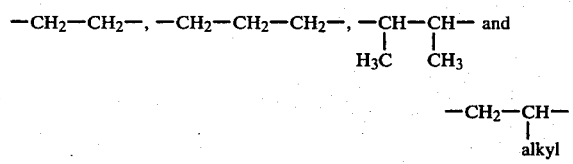

wherein said alkyl has from 1 to about 10 carbon atoms; and Ar is a member selected from the group consisting of phenyl, substituted phenyl, thienyl, halothienyl, naphthyl and fluorenyl, wherein "substituted phenyl" has the meaning of a phenyl radical having thereon from 1 to 3 substituents selected independently from the group consisting of halo, loweralkyl, loweralkyloxy, cyano and nitro.

The therapeutically active acid addition salts of the foregoing compound (I) are also embraced within the scope of this invention.

As used in the foregoing definition of Z, the term "alkyl" is meant to include straight and branch chained hydrocarbon radicals having from 1 to about 10 carbon atoms; such as, for example, methyl, ethyl, 1-methylethyl, propyl, 1,1-dimethylethyl, butyl, pentyl, hexyl, heptyl, octyl, decyl and the like; as used herein "loweralkyl" may be straight or branch chained saturated hydrocarbons having from 1 to 6 carbon atoms, such as, for example, methyl, ethyl, propyl, 1-methylethyl, butyl, 1,1-dimethylethyl, pentyl, hexyl and the like alkyls; and the term "halo" is generic to halogen atoms of atomic weight less than 127; i.e., fluoro, chloro, bromo and iodo.

The compounds of formula (I), in base form, may be converted to their therapeutically useful acid addition salts by reaction with an appropriate acid, as, for example, an inorganic acid such as hydrohalic acid, i.e., hydrochloric, hydrobromic or hydroiodic acid; sulfuric, nitric or thiocyanic acid; a phosphoric acid; an organic acid such as acetic, propanoic, hydroxyacetic, α-hydroxypropanoic, 2-oxopropanoic, ethanedioic, propanedioic, 1,4-butanedioic, (Z)-2-butenedioic, (D)-2-butenedioic, 2-hydroxy-1,4-butanedioic, 2,3-dihydroxy-1,4-butanedioic, 2-hydroxy-1,2,3-propanetricarboxylic, benzoic, 3-phenylpropenoic, α-hydroxybenzeneacetic, methanesulfonic, ethanesulfonic, hydroxyethanesulfonic, 4-methylbenzenesulfonic, α-hydroxybenzoic, 4-amino-2-hydroxybenzoic, 2-phenoxybenzoic or 2-acetyloxybenzoic acid. The salts are in turn converted to the corresponding free bases in the usual manner, e.g. by reaction with alkali such as sodium or potassium hydroxide.

From formula (I) it is evident that several of the compounds of this invention have asymmetric carbon atoms within their structure and consequently they may exist under different stereochemical optical isomeric forms. More particularly, when an alkyl group is present in the 4-position of the dioxolanenucleus, the carbon atoms to which it is attached and the carbon atom in the 2-position of the dioxolanenucleus are asymmetric. The stereochemical optical isomers of compounds of formula (I) may be separated and isolated following methodologies known to those skilled in the art. The use of said isomers is intended to be within the scope of this invention.

The compounds of formula (I) and the acid addition salts thereof are useful agents in combatting fungi and bacteria. As such the compounds are valuable in the treatment of plants and in the destruction of microorganism on materials.

The compounds are very potent agricultural fungicides. They are very active against a wide variety of fungi such as, for example, those responsible for the occurrence of powdery mildew on different plant species, e.g. *Erysiphe graminis, Erysiphe polygoni, Erysiphe cichorucearum, Erysiphe polyphaga, Podosphaera leuchotricha, Sphaerotheca punnosa, Sphaerotheca mors-urae, Uncinula necator*, etc., and other fungi, such as, for example, *Venturia inaequalis, Colletotrichum lindemuthianum, Fusarium oxysporum, Alternaria tenuis, Thielaviopsis basicola, Helminthosporium gramineum, Penicillium digitatum*, etc.

In the process of the invention the compounds (including the acid addition salts thereof) are coated on or impregnated into a substrate adapted to allow for vaporization of the compound and the substrate is positioned in relationship to the plant or plants to be treated at a distance and in a manner such that, due to the vapor action of the compound, the plant or plants have a reduced susceptibility to fungus attack. The compounds can, if necessary or desired, be coated or impregnated in suitable solvents or diluents in the form of solutions, suspensions, or dispersions, for example as taught in U.S. Pat. No. 4,079,062.

The preferred substrate is a substrate which retains substantial amounts of the compound, has a large effective surface area and preferably which allows air circulation through the substrate. An inert fabric is such substrate. Open weave substrates such as a "cheesecloth" weave are ideally suited as substrates. Plastic strips or sheets preferably perforated open cell foamaceous materials and the like are also useful. Solid carrier substances which are suitable for the preparation of compositions in powder form, such as discussed in U.S. Pat. No. 4,079,062 are also useful, especially where the powder, in turn, is employed on a substrate or in a container adapted for air circulation.

The amount of the compound employed is dependent, in part, on the area sought to be covered, the placement of the substrate in relationship to the plants, whether the space is enclosed, the air currents and the like. While the invention functions most suitably in a relatively closed space such as a greenhouse, it has application to open air crops as well. Routine experimentation with a particular substrate, a particular plant and a particular environment will readily determine the effective range of coverage by a particular substrate under the conditions present.

It is noted, for example, that shade tobacco is already covered with a cloth. Treatment of the cloth with the compounds described herein can be readily adapted.

The compounds of the invention are particularly useful in protecting plants such as apple trees, cucumbers, muskmelons, papaya, grapes, ornamental plants such as roses, and grains such as barley against fungal attack.

EXAMPLE I

This Example deals with the physical mode of action of seven of these chemicals, namely, 1-[[2-(2,4-dichlorophenyl)-4-ethyl-1,3-dioxolan-2-yl]methyl]-1H-1,2,4-triazole (Ciba-Geigy CGA 64251, Vanguard), biloxazol (Baycor), fenarimol (Eli Lilly EL 222), phenapronil (Rohm and Haas RH 2161), prochloraz (Boots-Hercules BFN 8206), triadimefon (Bayleton), and triforine (Funginex). These were evaluated rigorously in the laboratory and greenhouse on potted apple trees for their relative strengths and weaknesses in regard to (i) protection and tenacity, (ii) after-infection activity, (iii) presympton activity, and (iv) postsymptom activity against the apple scab pathogen *Venturia inaequalis* (Cke.) Wint., and in protective and vapor action against powdery mildew caused by *Podosphaera leucotricha* (Ell. & Ev.) Salm.

MATERIALS AND METHODS

Specific experimental procedures exploring each mode of action of fungicides are governed by conditions affecting the fungus pathogen. Under laboratory control of plant material, fungus inoculum, temperature, wetting, spraying, timing, etc., manipulation of each mode of action procedure was readily facilitated. The following sections on definition and procedure for each mode of action are brief as these were covered in detail elsewhere. (Azkolnik, N.Y. State Agric. Expt Sta., Spec. Report No. 28:22–27(1978); Szkolnik, *Annu. Rev. Phytophathol.*, 16:103–129 (1978)).

Apple scab—Protection (retention). In protection the fungicide is applied prior to or during an infection period so that the chemical can kill or inactivate the spores and prevent infection of the plant. The evaluative technique helps determine not only the protective mode of action of the fungicide at specific dosage rates but also its retentiveness on the leaf surface. A precision application of the dilute fungicidal spray was made at the rate of 10 mg of dilute spray of formulated fungicide per $cm^2$ of leaf surface. This deposit was vertified by weight on tared glass slides sprayed simultaneously with the trees of each treatment. This rate did not allow for runoff from the leaf. Following overnight drying, the trees received a 5-cm simulated overhead rainfall, and after 3 hours of drying they were mass innoculated with a suspension of 70,000 apple scab fungus conidia/ml applied with a paint sprayer. Ideal conditions for infection were provided in the mist chamber at 20° C. for 30 hours after which the trees were returned to the greenhouse for normal maintenance. Lesion counts were made two weeks after treatment.

After-infection. After-infection activity designates the capability of a fungicide applied at different times (hours, days) following infection to inhibit fungal development and prevent the establishment of scab lesions. This activity has also been referred to as eradication, curative action, kick-back, and intervention. In practice, each fungicide has been categorized according to the duration of after-infection activity measured from the beginning of the wet period because the start of wet conditions is much more precisely identified than is the calculated time of actual infection.

In the after-infection procedure the apple trees were mass inoculated and given an infection period in the mist chamber as described under protection. For fungicidal treatments made at specific times up to 30 hours following inoculation, the trees were withdrawn from the mist chamber at the desired time and immediately sprayed with the dilute fungicide. They were then returned to the greenhouse. For longer interval studies the trees, after a 30-hour infection period, were returned to the greenhouse and sprayed at the desired time interval. Freshly-sprayed trees were allowed to remain wet for a minimum of 15 minutes to allow for fungicidal effect. Scab lesion counts were made about 2 weeks after inoculation.

Presymptom activity. Presymptom activity is an elaboration of after-infection action. Some fungicides applied beyond their limit of after-infection activity have no meaningful effect on the development of typical olive-colored, sporulating scab lesions. Others so applied do not prevent lesion manifestation; however, the lesions are atypical and appear as chlorotic spots or flecks which produce few or no secondary conidia. This is defined as presymptom activity. Depending on the fungicide, dosage rate, and timing of spray, it is not unusual for presymptom activity to overlap with the actual after-infection activity.

This procedure calls for inoculation of apple trees as explained under protection. The dilute fungicidal spray was applied 5 to 7 days following inoculation and infection. This interval exceeds the after-infection limit of all fungicides tested in the greenhouse to date. Also, it precedes scab symptom appearance which, under greenhouse conditions, occurs 8 days or more following inoculation. Two weeks after inoculation the inoculated and sprayed leaves were collected. In the laboratory the spores were harvested with atomized water and counts of a standardized volume of spore suspension were made with a haemocytometer. Spore counts and the actual lesion count on the same leaves provided information on production of spores/lesion and, hence, the level of presymptom activity of the fungicide.

Postsymptom activity. In postsymptom activity, the fungicide applied to sporulating scab lesions prevents or greatly inhibits further production of new conidia from the same lesions.

In the postsymptom technique the apple trees were inoculated and given an infection period in the mist chamber as described for protection. Approximately two weeks later when abundant sporulating lesions were present on the foliage, the conidia were removed by the pressure of atomized water applied by a paint sprayer. Each fungicidal treatment was made as a dilute spray within 10 minutes of spore removal. About 3 days later the leaves were collected, the spores harvested and counted, and leaf lesion counts were made. The spores/lesion count revealed the postsymptom activity of fungicides tested.

Powdery mildew. McIntosh apple seedlings were used for these studies because they become readily infected with powdery mildew in the greenhouse and lesion counts are possible; more susceptible cultivars are prone to severe leaf distortions. The seedlings were first grown in greenhouse rooms where the relative humidity (RH) and inoculum level were usually too low for significant mildew development.

Protection. About 5 days prior to the start of cungicidal treatments, the potted trees were transferred to a "mildew greenhouse" where warm temperature and high humidity together with abundant inoculum from previously infected trees encouraged mildew infection. With the appearance of initial secondary mildew lesions on existing foilage, the youngest leaf on every tree was marked and the spray experiment initiated. Each fungicide was applied as a thorough dilute spray to the top and bottom surface of all elaves with a paint sprayer. The day following treatment, all the trees received a 7-mm overhead rainfall. This spray-rainfall procedure was repeated weekly for five consecutive weeks. At the time of the last spray the youngest leaf is marked, and after allowing at least five more days for full symptom expression, mildew lesion counts were taken on all the new leaves that developed during the course of the multiple spray program.

Vapor (fumigative) action. Initial tests on vapor action were conducted in closed fumigation chambers (*Phytopthology*, 70:469). The most effective mildewcide was later evaluated in larger scale greenhouse tests with a treated cheesecloth canopy over a large group of trees.

Fumigation Chambers. The circular fumigant action chamber was constructed of a plywood top and floor ring approximately 80 cm diameter with a vertical separation of 60 cm maintained by threaded rods. A flexible translucent fiberglass sheet of 60 cm width encircled the unit and the overlapped ends were kept in place with several spring hook catches. The open base of the chamber was placed on crushed stone on the greenhouse bench. Water seeping from a bleed irrigation hose (dew hose) embedded in the crushed stones kept the stones wet, thus maintaining 100% RH within the enclosed chamber throughout the period of the test.

At the start of the test, several pots of essentially mildew-free trees received a dilute spray of the test fungicide and were placed immediately in the fumigation chamber. Other mildew-free trees without treatment (including water) were placed into the chambers but not in direct contact with the sprayed trees. Mildewed trees were also placed into the chamber to provide inoculum. Just before closing the fumigation chamber, all trees received a liberal inoculation by blowing spores onto them from dry seedlings with abundant new infections. The trees were kept in the closed chamber 2 to 4 days and then returned to a mildew-free house where lesions counts were made approximately one week later on the youngest susceptible leaves which were exposed to the fungicide vapor.

Fumigation Canopy. In these studies the fungicide with the most consistent record of effective mildew control in the fumigation chambers, CGA 64251, was used. In the two experiments reported here, McIntosh apple seedlings relatively free of powdery mildew were transferred to the "mildew greenhouse" on the day of treatment. A wooden framework over the trees made it possible to stretch a pretreated cheesecloth on it to form a canopy over the top and two sides of a group of trees. Two sides were left open. Approximately 50 15-cm pots of three seedlings each and occupying a greenhouse bench area of 140×180 cm comprised the treatment group with a similar number in the control group.

The cheesecloth was first soaked in a suspension of the fungicide and the excess squeezed out to prevent any drip of the fungicide directly onto the trees. This cheesecloth was immediately stretched and stapled onto the wooden framework to form the canopy with the top approximately 15 cm above the top of the tallest seedlings. In similar manner cheesecloth was soaked in distilled water, squeezed out, and stretched onto a frame over control trees on the bench adjacent to the chemical treatment group. Just prior to placement of the canopy, all trees of both groups were inoculated liberally by blowing spores onto them from dry, heavily-mildewed trees. A large number of infected trees in the greenhouse room was misted overnight the day of treatment and 2 days later. After 2 weeks, the cheesecloth canopies were removed and powdery mildew leaf lesion counts made.

RESULTS AND DISCUSSION

Comparison of fungicidal performance in controlling apple scab shown in the composite table of results (Table 1) is facilitated by the use of a whole number "control rating" ranging from 0 to 10 with 0 representing complete control. This rating, developed from a $\log_{10}$ paper and an arbitrary "0", provides a weighed comparison of fungicidal efficacy. A "control rating" is calculated from the raw lesion counts for each treatment in each experiment based on the severity of scab on the water-sprayed control trees in that experiment. The control rating for each fungicide in the tables is the average for a minimum of three experiments in each mode of action category. The minimum percent control for control ratings 0, 1, 2, etc. is 100, 98, 94, 89, 83, 76, 68, 59, 47, 29, and 0, respectively.

TABLE 1

Fungicidal modes of action against apple scab. Ratings for retention and after-infection denote control of scab lesion development; those for pre- and postsymptom denote inhibition of spore production from scab lesions.

| Treatment | Dose (a.i.) (μg/ml) | Disease control or spore inhibition rating[a] | | | |
|---|---|---|---|---|---|
| | | Retention | After-infection | Pre-symptom | Post-symptom |
| Water | — | 10 | 10 | 10 | 10 |
| Mancozeb | 1 | 10 | 10 | 9 | |
| Captan | 1200 | 2 | 10 | 10 | 10 |
| Dodine | 293 | 2 | 7 | tr | 1 |
| Dichlone | 150 | 3 | 5 | 9 | 1 |
| Glyodin | 720 | 3 | 10 | 10 | 1 |
| Phenylmercuric acetate | 30 | 4 | tr | 0 | 1 |
| CGA 64251 | 30 | 4 | tr | 0 | 10 |
| Benomyl | 225 | 7 | 7 | 0 | 1 |
| Fenarimol | 40 | 9 | tr | 0 | 10 |
| Biloxazol | 300 | 9 | 6 | tr | 10 |
| Triadimefon | 300 | 9 | 6 | tr | 10 |
| Phenapronil | 300 | 9 | 5 | 1 | 10 |
| Triforine | 167 | 10 | 5 | 2 | 10 |
| Prochloraz | 300 | 10 | 8 | 0 | 10 |

[a]Minimum percent disease control or spore inhibition for ratings 0, 1, 2, etc. is 100, 98, 94, 89, 83, 76, 68, 59, 47, 29, and 0, respectively.
tr = trace, >99.5 percent.

Protection (retention). Sterol-inhibiting fungicides in general were weak to ineffective protectants against apple scab (Table 1). With control ratings of 4 to 10, their protective action was decidedly inferior to that of manoczeb, captan, dodine, dichlone and glyodin which were in the 1 to 3 control rating range. One of the sterol inhibitors stands uniquely apart from the others in protection, namely, CGA 64251, which at 30 ug/ml gives a fairly good measure of protection (control rating, 4) compared with fenarimol, biloxazol, triadimefon, phenapronil, triforine, and prochloraz which, at active rates of 167 to 300 ug/ml, gave very little or no meaningful protection against scab. The fungicide retention technique depends highly on the kill or insactivation of spores. Most of the sterol inhibitors tested did not effectively prevent conidial germination and, therefore, did not prevent infection.

After-infection. The after-infection activity of sterol inhibitors exceeded that of protection (Table 1). In this mode of action they outperformed standard fungicides like mancozeb, captan, and glyodin whose strength lies largely in protection against apple scab. CGA 64251 and ferarimol showed a potency equivalent to that of phenylmercuric acetate, the unique eradicative fungicide used in apple orchards for two decades preceding discontinuance by regulatory action about 1971. In fact, these two sterol inhibitors exceeded the performance of 30 ug/ml phenylmercuric acetate in applications 2 and 3 days following inoculation (Table 2). The eradicative potency of the organic mercurials has not been equalled heretofore by any approved fungicide. Other sterol inhibitors, although less effective than the CGA 64251 and fenarimol, had an after-infection potency equivalent to that of dichlone. Dichlone is the most effective after-infection scab fungicide among all fungicides currently approved for use on apple.

TABLE 2

After-infection mode of action of fungicides applied 1 to 3 days following inoculation in the control of apple scab.

| Treatment | Dose (a.i.) (μg/ml) | Scab control rating[a] for spray applied at: | | |
|---|---|---|---|---|
| | | 1 day | 2 days | 3 days |
| Water | — | 10 | 10 | 10 |
| CGA 64251 | 30 | tr | 1 | tr |
| Fenarimol | 40 | 1 | tr | tr |
| Phenylmercuric acetate | 30 | tr | 2 | 7 |
| Phenapronil | 300 | 5 | 4 | 6 |
| Dichlone | 150 | 5 | 8 | 10 |
| Triforine | 167 | 5 | 8 | 9 |
| Biloxazol | 300 | 6 | 7 | 8 |
| Triadimefon | 300 | 6 | 8 | 10 |
| Dodine | 293 | 7 | 8 | 10 |
| Benomyl | 225 | 7 | 8 | 9 |
| Prochloraz | 300 | 8 | 7 | 10 |
| Captan | 1200 | 10 | 9 | 10 |

[a]Minimum percent disease control for ratings 0, 1, 2 etc. is 100, 98, 94, 89, 83, 76, 68, 59, 47, 29, and 0, respectively.
tr = trace, >99.5 percent.

Presymptom. All seven sterol inhibitors tested shared with dodine and benomyl a high level of presymptom activity (Table 1). This activity was lacking in captan, mancozeb, dichlone, and glyodin. Evidently the sterol inhibitors have a potent and adverse action against the established scab fungus mycelium during the incubation period. Different rates of the sterol inhibitors have not yet been fully evaluated for presymptom activity, but indications are that this level of activity is proportionate to the active rate of the toxicant as has been demonstrated for dodine and benomyl. The specific benefit derived from presymptom activity comes from a great reduction in secondary scab inoculum which then reduces the pressure on fungicidal sprays applied later. Presymptom activity has been recognized in the orchard performance of fungicides, but further studies need to be made to more clearly define the value of this activity as influenced by such factors as dosage rates, timing, moisture requirements, duration of incubation periods, redistribution of fungicides, and effective threshold levels.

Postsymptom. All seven sterol inhibitors tested failed in postsymptom activity against apple scab (Table 1). Continued production of conidia from existing active scab lesions was not abated by these fungicides, which is in sharp contrast to their presymptom activity. They differed greatly from dodine, benomyl, phenylmercuric acetate, dichlone, and glyodin which performed effectively in the postsymptom mode of action. Among the fungicides evaluated only dodine, benomyl, and phenylmercuric acetate were very active in both the presymptom and postsymptom modes of action. Unfortunately, dodine and benomyl are prone to pathogen resistance. As noted above, the benefit from postsymptom activity lies in the reduction of pathogen inoculum pressure and improvement of chances for better scab control with succeeding sprays.

For powdery mildew, biloxazol, triadimefon, and CGA 64251 applied weekly as a dilute spray were highly effective in protecting apple foliage (Table 3). Control of mildew was greater than that obtained with standard mildewcides sulfur, benomyl, and dinocap. That differences in efficacy within the family of sterol inhibitors do occur was evident from the lower activity of triforine which provided control equivalent to that of dinocap rather than to that of the three sterol inhibitors noted above.

TABLE 3

Fungicidal protective action in the control of apple powdery mildew.

| Treatment | Dose (a.i.) (μg/ml) | % Leaves with powdery mildew |
|---|---|---|
| Water | — | 100 |
| Biloxazol | 150 | 1 |
| Triadimefon | 150 | 1 |
| CGA 64251 | 20 | 2 |
| Sulfur | 900 | 6 |
| Dichlone | 300 | 18 |
| Benomyl | 225 | 23 |
| Triforine | 167 | 49 |
| Dinocap | 75 | 50 |
| Captan | 1200 | 99 |

A "growth regulator" response was evident on seedlings receiving repeated applications of CGA 64251. The plants were shorter than those receiving other effective mildewcides. The leaves were also smaller, somewhat cupped, less flexible, and darker green than those of other treatments. These responses were not observed on apple trees in the apple scab experiments involving just a single application of the sterol inhibitors.

Within the enclosed fumigation chambers, the chemical vapor emission from trees sprayed with either CGA 64251 or triadimefon gave substantial protection to untreated trees in the same chamber against powdery mildew (Table 4). Marked differences in vapor action among sterol inhibitors was evident by the occurrence of only three or four mildew lesions per leaf with the ones noted above compared with 17 lesions for fenarimol and 41 for triforine. The fenarimol activity was about the same as with sulfur, while the triforine was about as inactive in this mode of action as was dinocap. No growth regulator response was observed on either sprayed trees or the untreated trees exposed to the chemical vapor inside the chamber. Although it is common knowledge that sulfur vapor controls powdery mildew, it appears that temperatures higher than the 23° C. prevalent in these fumigation chambers would be needed for greater activity by sulfur.

TABLE 4

Vapor action of fungicides in a closed fumigation chamber in the protection of apple trees against powdery mildew. The data are from untreated trees in the same chamber with those treated but not in contact.

| Treatment | Dose (a.i.) (μg/ml) | Powdery mildew | |
|---|---|---|---|
| | | % Leaves infected | Lesions per leaf |
| Water | — | 99 | 50 |
| CGA 64251 | 7.5 | 56 | 3 |
| Triadimefon | 18.8 | 59 | 4 |
| Sulfur | 900.0 | 87 | 13 |
| Fenarimol | 9.4 | 92 | 17 |
| Dinocap | 75.0 | 90 | 27 |
| Triforine | 83.7 | 98 | 41 |

The CGA 64251-impregnated cheesecloth canopy, although not forming a closed chamber, allowed for an ample vapor environment among the trees below to provide substantial mildew control in contrast to the high level of mildew on trees beneath the adjacent canopy without chemical treatment (Table 5). Not only were fewer leaves infected but the number of lesions per infected leaf were greatly reduced under the canopy treated with the sterol inhibitor. There was no evidence of growth regulator effect from the chemical vapor. The favorable results suggest realistic benefits from vapor activity of sterol inhibitors in the control of powdery mildew diseases in the greenhouse and under certain circumstances in the field.

TABLE 5

Vapor action of CGA 64251 from a pretreated cheesecloth canopy for control of powdery mildew on untreated apple trees in the greenhouse.

| Treatment of cheesecloth canopy | Powdery mildew | |
|---|---|---|
| | % Leaves infected | Lesions per leaf |
| Test I | | |
| Water | 88 | 29 |
| CGA 64251, 30 ppm | 64 | 12 |
| Test II | | |
| Water | 75 | 19 |
| CGA 64251, 30 ppm | 40 | 3 |

CONCLUSIONS

The sterol synthesis inhibitors are broad-spectrum fungicides. In addition to the activity reported here against apple scab and powdery mildew, several of these chemicals provided good to excellent protective, after-infection, or presymptom activity against cedar-apple rust incited by *Gymnosporangium juniperi-virginianae* and cherry leaf spot incited by *Coccomyces hiemalis* (Gilpatrick et al, Fung. and Nemat. Tests, 35:30–31; Hickey et al, Fung. and Nemat. Tests, 35: (6–7). They also provide excellent control of brown rots of stone fruits incited by *Monilinia fructiocola* through both protective and after-infection activity (Gilpatric et al, supra). Such activity against a number of unrelated fungal pathogens stresses the potency of the sterol-inhibiting action. The broad spectrum also suggests that other biochemical modes of action may be involved.

EXAMPLE II

The sterol-inhibiting fungicides Ciba-Geigy CGA 64251, triadimefon (Bayleton), fenarimol (Eli Lilly EL 222), and triforine (Cela-Merck CME 74770) were compared with dinocap (Karathane), sulfur, and water in closed fumigative chambers for vapor phase activity against apple powdery mildew. Circular chambers of plywood framework were constructed comprised of a full top and an open bottom. Threaded rods maintained the height of the chamber. A flexible translucent fiberglass sheet encircled the framework and was held together at the loose ends by spring catches.

With the open bottom of the chamber resting on crushed stone on a greenhouse bench, the moisture from the stones, kept wet by buried bleed-irrigation tubes, maintained a constant 100% relative humidity in the fumigation chamber. This humidity together with the temperature of 22° C. (72° F.) was ideal for powdery mildew infections. Fumigation chambers in this work were 79 cm (31 inches) in diameter and 61 cm (24 inches) high. These held 12 15-cm (6-inch) clay pots of 5 McIntosh seedlings each. The seedlings had 10 to 13 leaves. Three pots of untreated seedlings were placed in the center of each chamber surrounded by 7 pots; of the latter, 2 were mildew-infected and sporulating as a source of inoculum. The fungicide under test was sprayed outside the chamber, onto the foliage of the 5 pots of trees which were then placed into the chamber. With the trees in place the fumigation chamber was closed. After a 2-day exposure in the chamber the trees were returned to a greenhouse room relatively free of powdery mildew until data were taken approximately a week later. Unusual control of mildew was obtained from the vapors of the sterol inhibitors Ciba-Geigy CGA 64251 and triadimefon (Bayleton). Fenarimol and sulfur were moderately effective, whereas Karathane and triforine were not. No foliar injury was detected from any of the fungicide vapors.

| Fungicide product and rate per 100 gal. | Active ppm | Leaves Infected (%) | Mildew lesions per leaf |
|---|---|---|---|
| Water | — | 99 | 50 |
| Ciba-Geigy CGA 64251 10W 1.0 oz | 7.5 | 56 | 3 |
| Bayleton 50W 0.5 oz | 18.8 | 59 | 4 |
| Super Six Sulfur 6F 1.0 pt | 900.0 | 87 | 13 |
| Eli Lilly EL 222 12.5EC 1.0 oz | 9.4 | 92 | 17 |
| Karathane 25W 4.0 oz | 75.0 | 90 | 27 |
| Cela-Merck CME 74770 18.6EC 6.0 oz | 83.7 | 98 | 41 |

EXAMPLE III

Circular chamber plywood framework were constructed comprised of a full top and an open bottom, except for a necessary structural base ring. Threaded rods maintained the height of the chamber. A flexible translucent fiberglass sheet encircled the framework and was held together at the loose ends by spring catches. Initial tests were done on apple powdery mildew. With the open bottom of the chamber resting on crushed stone on a greenhouse bench, the moisture from the stones wet by buried bleed-irrigation tubes, maintained a constant 100% relative humidity in the fumigation chamber. This humidity, together with the temperature at 72° F. (22° C.) was ideal for powdery mildew infections. Fumigation chambers in this work were 31 inches (79 cm) in diameter and 24 inches (61 cm) high and held 12 6-inch (15 cm) clay pots of 5 McIntosh seedlings each. The seedlin had 10 to 13 leaves. Three pots of untreated seedlings were placed in the center of each chamber surrounded by 7 pots; of these, 2 were mildew-infected and sporulating as a source of inoculum. The fungicide under test was sprayed onto the foliage of the 5 pots of trees or to an equivalent area of cheesecloth. The sprayed cheesecloth was suspended horizontally above on a rack supported by wires. With trees or cheesecloth in place, the fumigation chamber was closed; and and after a desired time exposure the trees were removed to a greenhouse room relatively free of powdery mildew until data were taken on untreated trees.

Unusual control of mildew was obtained from the vapors of Ciba Geigy CGA 64251, a new broad-spectrum triazole fungicide. No injury to the foliage observed.

| Treatment and rate (ppm) ai | Spray applied to | Days in Fumigation chamber | Mildew lesions on untreated foliage |
|---|---|---|---|
| TEST A | | | |
| CGA 64251 45.0 | foliage | 4 | 1 |
| CGA 64251 45.0 | foliage | 7 | trace |
| CGA 64251 45.0 | cloth | 4 | 1 |
| CGA 64251 45.0 | cloth | 7 | trace |
| Water | foliage | 7 | 8 |
| TEST B | | | |
| CGA 64251 30.0 | foliage | 2 | trace |
| CGA 64251 30.0 | foliage | 4 | 1 |
| CGA 64251 7.5 | foliage | 2 | 4 |
| CGA 64251 7.5 | foliage | 4 | trace |
| Water | foliage | 2 | 18 |
| Water | foliage | 4 | 12 |

EXAMPLE IV

Control of Apple Powdery Mildew by Vapor from a New Triazole Fungicide. Michael Szkolnik, Dept. of Plant Pathology, New York State Agricultural Experiment Station, Geneva 14456 Nov. 1979. 1-[[2-(2,4-dichlorophenyl)-4-ethyl-1,3-dioxolan-2-yl]methyl]-1H-1,2,4-triazole (Ciba-Geigy CGA 64251) applied to McIntosh apple foliage controlled powdery mildew (Podosphaera leucotricha) on untreated apple seedlings in same greenhouse fumigation chamber. In the center of each round fiberglass chamber (287 l) were 3 pots, each with 5 untreated seedlings of 16 cm height and 11 leaves. Surrounding these were 7 pots of trees whose 3100 cm$^2$ leaf area was sprayed with 90 ml of dilute fungicide, and 2 pots of mildewed trees for inoculum. In one test untreated trees in the presence of those sprayed with 30 or 45 ppm active CGA 64251 for 5 days developed only 1 mildew lesion per leaf compared with 30 lesions in an adjacent chamber without the chemical. In a second test untreated trees in the chambers 4 days with trees sprayed with 7.5 or 30 ppm CGA 64251 developed 1 lesion per leaf compared with 18 lesions in the control chamber. A 2-day exposure at these rates gave nearly as good control. Vapor from CGA 64251-treated cheesecloth suspended on wire above untreated trees also gave excellent control.

EXAMPLE V

Cheesecloth treated once with 1-[[2-(2,4-dichlorophenyl)-4-ethyl-1,3-dioxolan-2-yl]methyl]-1H-1,2,4-triazole (Ciba-Geigy CGA 64251, Vanguard) was suspended as a curtain along the center of a 112 m$^3$ greenhouse room. The 384 mg (a.i.) of the fungicide in the 6 m$^2$ cheesecloth was equivalent to 3.43 mg per m$^3$ of room. On the same date and at weekly intervals, pair groups of plants inoculated with powdery mildew spores were placed in this house and in an untreated house. Temperature above 20° C. and RH above 90% in both houses favored mildew. In the untreated house severe mildew occurred on all McIntosh apple seedlings inoculated with Podosphaera leucotricha and on all muskmelon and cucumber plants inoculated with Sphaerotheca fuliginea. In the treated house both hosts remained free of powdery mildew for at least 20 weeks. This control is attributed to vapor action by CGA 64251. Continued control on plants set into the treated house even 9 weeks after the treated cloth was set in place proved persistence of vapor effectiveness.

I claim:

1. A method of protecting plants from fungal attack or reducing the severity of fungal attach which comprises positioning a substrate coated or impregnated with 1-[[2-(2,4-dichlorophenyl)-4-ethyl-1,3-dioxolan-2-yl]methyl]-1H-1,2,4-triazole in an amount and in a manner such that vapors of said triazole cause said protection from or reduction of fungal activity on the plants.

2. The method of claim 1 where the substrate is a fabric sheet.

3. The method of claims 1 or 2 where the method is conducted in an enclosure.

4. The method of claim 13 where the substrate is a fabric sheet.

5. The method of claims 1 or 2 where the fungus protected against is the caustive agent for powdery mildew.

6. An article comprising a substrate having a large effective surface area and which allows air circulation therethrough having coated thereon or impregnated therein 1-[[2-(2,4-dichlorophenyl)-4-ethyl-1,3-dioxolan-2-yl]methyl]-1H-1,2,4-triazole, said coated or impregnated substrate being selected from the group consisting of a fabric, a foamaceous material and a powder in a container which allows air circulation therethrough, said coated or impregnated substrate capable of providing a fungicidally effective vapor of said triazole.

7. The article of claim 6 where the substrate is a fabric.

* * * * *

UNITED STATES PATENT AND TRADEMARK OFFICE
CERTIFICATE OF CORRECTION

PATENT NO. : 4,391,813
DATED      : July 5, 1983
INVENTOR(S) : Michael Szkolnik

It is certified that error appears in the above-identified patent and that said Letters Patent is hereby corrected as shown below:

Column 12, line 65, "attach" should read -- attack --.

Column 13, line 8, "13" should read -- 3 --.

Signed and Sealed this

Twenty-seventh Day of September 1983

[SEAL]

Attest:

GERALD J. MOSSINGHOFF

Attesting Officer        Commissioner of Patents and Trademarks